United States Patent [19]

Olson

[11] 4,312,359
[45] Jan. 26, 1982

[54] NONINVASIVE BLOOD PRESSURE MEASURING SYSTEM

[75] Inventor: Theodore A. Olson, Minneapolis, Minn.

[73] Assignee: Life Care Systems, Inc., Minneapolis, Minn.

[21] Appl. No.: 122,371

[22] Filed: Feb. 19, 1980

[51] Int. Cl.³ .............................................. A61B 5/02
[52] U.S. Cl. ..................................... 128/680; 128/682
[58] Field of Search .............................. 128/677–686, 128/689–690; 364/415–417

[56] References Cited

U.S. PATENT DOCUMENTS

| | | | |
|---|---|---|---|
| D. 250,896 | 1/1979 | Huber | 128/677 X |
| 3,308,811 | 3/1967 | Gillette et al. | 128/680 |
| 3,374,461 | 3/1968 | Anderholm et al. | 128/671 |
| 3,400,709 | 9/1968 | Funfstuck | 128/672 |
| 3,405,707 | 10/1968 | Edwards | 128/680 |
| 3,550,582 | 12/1970 | Wilhelmson | 128/683 |
| 3,552,381 | 1/1971 | Burns et al. | 128/683 |
| 3,581,734 | 6/1971 | Croslin et al. | 128/679 |
| 3,654,915 | 4/1972 | Sanctuary | 128/682 |
| 3,717,140 | 2/1973 | Greenwood | 128/684 |
| 3,744,490 | 7/1973 | Fernandez | 128/683 |
| 3,773,033 | 11/1973 | Robard et al. | 128/687 |
| 3,779,235 | 12/1973 | Murphy, Jr. et al. | 128/682 |
| 3,814,083 | 6/1974 | Fletcher et al. | 128/683 |
| 3,850,169 | 11/1974 | Gebben et al. | 128/687 |
| 3,858,574 | 1/1975 | Page | 128/666 |
| 3,905,354 | 9/1975 | Lichowsky | 128/681 |
| 3,920,004 | 11/1975 | Nakayama | 128/680 |
| 4,009,709 | 3/1977 | Link et al. | 128/681 |
| 4,011,860 | 3/1977 | Lee | 128/683 |
| 4,026,277 | 5/1977 | Toda et al. | 128/681 |
| 4,033,336 | 7/1977 | Murawski et al. | 128/682 |
| 4,069,815 | 1/1978 | Lee | 128/683 |
| 4,105,020 | 8/1978 | Matsuoka et al. | 128/682 |
| 4,112,491 | 9/1978 | Bugay | 128/687 |
| 4,116,230 | 9/1978 | Gowlick | 128/682 |
| 4,216,779 | 8/1980 | Squires et al. | 128/682 |

OTHER PUBLICATIONS

Georgi H., "Electronic Sphygmomanometer", GB 2006, 961, publ. May 1979.

Primary Examiner—Robert W. Michell
Assistant Examiner—Francis J. Jaworski
Attorney, Agent, or Firm—Kinney, Lange, Braddock, Westman and Fairbairn

[57] ABSTRACT

A noninvasive blood pressure measuring system includes an inflatable cuff for encircling a portion of the human body. The cuff is inflated to a pressure sufficient to occlude arterial flow, and the pressure is then released by opening of a pressure relief valve for short periods of time to reduce the pressure until both the systolic and diastolic events have occurred. The incremental decrease in pressure with each opening of the pressure relief valve is controlled by monitoring the pressure before opening and after closing the pressure relief valve. The time duration of the next valve opening cycle is controlled as a function of the comparison of the two pressures so as to maintain an average incremental decrease in pressure. In addition to systolic and diastolic blood pressures, pulse rate is also determined by counting the number of pulses between the systolic and diastolic events and determining the time elapsed between the two events. After occurrence of the systolic event, the valve is opened between pulses and the microphone and signal processing circuitry are disabled during the valve opening to prevent valve noise from creating false pulse signals.

18 Claims, 4 Drawing Figures

NONINVASIVE BLOOD PRESSURE MEASURING SYSTEM

BACKGROUND OF THE INVENTION

1. Field of the Invention

The present invention relates to noninvasive blood pressure measuring apparatus. In particular, the present invention is related to automatic noninvasive apparatus for providing measurement of systolic and diastolic blood pressures and pulse rate.

2. Description of the Prior Art

The most common method for determining blood pressure utilizes the Korotkoff sound technique. In this technique, an inflatable cuff is placed around the upper arm of a person and is inflated until the underlying artery is occluded. Pressure is then released gradually from the cuff until blood begins to pass through the artery. This passage of blood through the partially occluded artery produces Korotkoff sounds which may be detected by the use of a stethoscope or, in automated systems, by the use of a microphone. By monitoring the Korotkoff sounds and the cuff pressure, the systolic and diastolic pressures may be determined.

Systolic pressure is the pressure within the cuff at the time when a sudden increase in the intensity of Korotkoff sounds occurs. Diastolic pressure is the pressure at which a sudden reduction in intensity in Korotkoff sounds occurs.

While the detection of systolic and diastolic pressure can be performed manually, automation of this technique is clearly advantageous. Recently a number of automated blood pressure measuring systems have been developed. In many cases, these automated systems determine not only systolic and diastolic pressures, but also the pulse rate of the individual.

The following patents describe a variety of automatic or semi-automatic noninvasive blood pressure and pulse rate measuring devices. In most cases, the devices operate utilizing the Korotkoff technique.

Gillette et al U.S. Pat. No. 3,308,811 shows blood pressure measuring apparatus which processes the sounds from the microphone by passing the output of the microphone through a filter which passes a first band of frequencies until the systolic pressure is determined. The characteristics of the filter are then changed to pass a second band of frequencies which permit the diastolic pressure to be determined more accurately.

Anderholm et al U.S. Pat. No. 3,374,461 shows a physiological monitoring system which includes a transducer 23 for measuring both systolic and diastolic pressure and a transducer 24 for measuring pulse rate. The patent states (in column 5, lines 15-20) that pulse rate transducer 24 can be a separate transducer or the pulse rate can be measured by transducer 23. As described in column 9, lines 33-45, a logical AND circuit 199 is provided to ensure that the first indication of systolic pressure is not merely an artifact. After the first pulse rate is detected, another pulse must be sensed within two seconds if true systolic pressure has been sensed.

Funfstuck U.S. Pat. No. 3,400,709 shows a blood pressure monitor which uses a strain-gauge to produce a signal consisting of a DC signal responsive to the static blood pressure on which is superimposed an AC signal. The peak value of the AC signal is the systolic pressure and the negative peak of the AC wave is the diastolic pressure.

Edwards U.S. Pat. No. 3,405,707 shows a blood pressure measuring apparatus including a distinguishing system which responds to the difference between the energy level of the Korotkoff sounds and the noise level.

Wilhelmson U.S. Pat. No. 3,550,582 shows a portable blood pressure monitor. A cuff is inflated until the diastolic pressure is exceeded and the first Korotkoff sounds are sensed. The pressure in the cuff is then released until no further Korotkoff sounds are sensed (i.e. the pressure is below the diastolic pressure).

Burns et al U.S. Pat. No. 3,552,381 describes a technique for measuring diastolic blood pressure. A pressure is applied to the cuff which is sufficient to cut off arterial flow and negative-going pressure pulses are then applied which momentarily relieve the applied pressure in the cuff by predetermined amounts. These negative-going pulses are timed to coincide with the pressure minima of each pulse. Diastolic pressure is sensed when the pulse pressure minima overlaps sufficiently with the relieved applied pressure to permit spurts of arterial flow.

Croslin et al U.S. Pat. No. 3,581,734 shows a blood pressure measuring apparatus using a pair of cuffs, one for occluding the artery and the other for sensing. The systolic pressure is indicated only if a second pulse is detected within an expected time interval or window after a first detected pulse and if the second pulse is larger than the first pulse. After the systolic pressure has been sensed, the amplitude of each successive pulse is detected and the peak value is stored. The diastolic pressure is indicated after the systolic pressure has been sensed and only after a pulse is detected which has a peak value less than 0.7 of the largest peak value which has been detected and stored.

Sanctuary U.S. Pat. No. 3,654,915 shows a blood pressure measuring apparatus using a mercury column manometer and contacts for sensing the level of the mercury each time a Korotkoff sound signal is detected. Signal processing eliminates artifacts including Korotkoff sound signals which were neither preceded nor succeeded by another sound signal. Greenwood U.S. Pat. No. 3,717,140 shows a pulse rate measuring device including a counter which counts clock pulses between consecutive heart beats. The number of clock pulses counted is used to determine the pulse rate which is displayed.

Fernandez U.S. Pat. No. 3,744,490 shows a blood pressure measuring system which senses the systolic and diastolic pressures both on inflation and on deflation of the cuff. The electrical impedance between two body locations is also sensed and is used in controlling the valve for inflation and deflation of the cuff.

Rodbard et al U.S. Pat. No. 3,773,033 shows apparatus in which inputs are received from ECG electrodes, from a heart sound microphone, and from an arterial vibration sensor. The output of the system is displayed on a cathode ray tube.

Murphy, Jr. et al U.S. Pat. No. 3,779,235 describes an interface circuit which converts signals from a pressurometer to serial binary data representative of patient pulse rate and patient systolic and diastolic blood pressures.

Fletcher et al U.S. Pat. No. 3,814,083 shows a Korotkoff sound processor.

Gebben et al U.S. Pat. No. 3,850,169 shows analog circuitry for processing arterial pressure waveforms to detect the initial systole and dicrotic notch.

Page U.S. Pat. No. 3,858,574 shows a pulse rate meter which provides both a visual indication of each pulse beat and a digital readout of the pulse rate of a patient.

Nakayama U.S. Pat. No. 3,920,004 shows a noninvasive device which measures not only blood pressure, but also a variety of other parameters relating to blood flow.

Link et al U.S. Pat. No. 4,009,709 describes a technique in which the systolic pressure is sensed by phasing the pressure in a pressure cuff and measuring a quantity proportional to a time dependent fluctuating component representative of pulsatile pressure within the blood vessel. The systolic pressure is equal to the applied cuff pressure when the fluctuating quantity is about equal to one-half its maximum value.

Toda et al U.S. Pat. No. 4,062,277 shows a blood pressure measuring apparatus having two band-pass filters to separate the signal from the microphone into Korotkoff sounds and Sphygmus sounds. The systolic pressure is determined when two or more Korotkoff sounds correspond to the occurrence of the Sphygmus sounds. Similarly, the diastolic pressure is determined when Korotkoff sounds do not appear at successive times while Sphygmus sounds do occur.

Murawski et al U.S. Pat. No. 4,033,336 shows a system for sensing a variety of different medical characteristics. The system includes a blood pressure sensor shown in FIG. 14 and described in columns 17 through 20. The patent states that the cuff is gradually deflated at a predetermined rate by bleed valve 472, but provides no description of how the rate would be maintained constant.

Lee U.S. Pat. No. 4,069,815 provides a linear or uniform decline in pressure of the cuff during the deflation portion of the cycle. A constant volume reference container having rigid walls is linearally pressurized and depressurized with air to regulate the linear pressurizing and depressurizing of the flexible cuff.

Matsuoka et al U.S. Pat. No. 4,105,020 shows apparatus in which both pulse rate and blood pressure are measured automatically. The apparatus includes a pulse sound filter and a Korotkoff sound filter. The pulse rate measuring circuit commences counting pulses after at least two Korotkoff sounds have been detected. This counting continues until a predetermined number is reached. The pulse rate is determined by dividing the predetermined number by the time period required to count the predetermined number of pulses. The patent also describes an alternative embodiment in which the pulse sound signals are counted for a predetermined time period, and the number of pulses counted is divided by the predetermined time.

Lee U.S. Pat. No. 4,011,860 describes calibration of the pressure sensor in a blood pressure measuring system. A recalibration cycle occurs at the outset of each blood pressure measurement. During recalibration, a reference pressure is maintained and the output signal is adjusted until a reference level is reached.

Bugay U.S. Pat. No. 4,112,491 shows an analog computer which determines and displays pulsatile flow.

Huber et al U.S. Pat. No. D250,896 is a design patent showing a coin operated automatic blood pressure testing apparatus.

SUMMARY OF THE INVENTION

The present invention is a noninvasive blood pressure measuring system for automatically determining systolic and diastolic pressures of an individual. The system includes an inflatable cuff for encircling a portion of the body of the individual. Inflating means inflate the cuff to a pressure sufficient to occlude arterial flow. Pressure relief valve means is provided which is opened periodically for controlled time durations to deflate the cuff by pressure increments.

Since the cuff will have a higher pressure initially, the same time duration of opening would result in a greater incremental pressure change when the cuff pressure is higher than when the cuff pressure is lower. In the present invention, this problem is overcome by sensing the cuff pressure and comparing the sensed cuff pressure before and after each opening cycle of the pressure relief valve means. The time duration of a subsequent valve opening cycle is controlled as a function of the comparison of the sensed pressure so as to maintain an average pressure decrease increment.

The present invention also preferably provides a signal indicative of pulse rate as well as signals indicative of systolic and diastolic pressures. To determine pulse rate, the number of pulse signals provided between occurrence of the systolic and diastolic events is counted and the time elapsed between those events is determined. The pulse rate is a function of the number of pulse signals counted and the elapsed time.

The present invention also preferably includes means for synchronizing the operation of the pressure relief valve means and the signal processing circuitry to avoid noise problems associated with the opening of the pressure relief valve. In a first mode of the operation, the pressure relief valve is opened at predetermined time periods. Upon detection of the systolic pressure, the operation of the apparatus changes to a second mode. In this second mode, the opening of the valve is synchronized with the detection of the pulse of the individual. The microphone and the signal processing circuitry is disabled beginning at a predetermined time period after occurrence of a pulse and continues to be disabled for a predetermined time interval. During this predetermined time interval, the pressure relief valve means is opened to reduce pressure in the cuff. By disabling the microphone and signal processing circuitry, noise associated with opening and closing of the valve is precluded from creating false pulse signals.

DETAILED DESCRIPTION OF THE PREFERRED EMBODIMENTS

Figure 1:
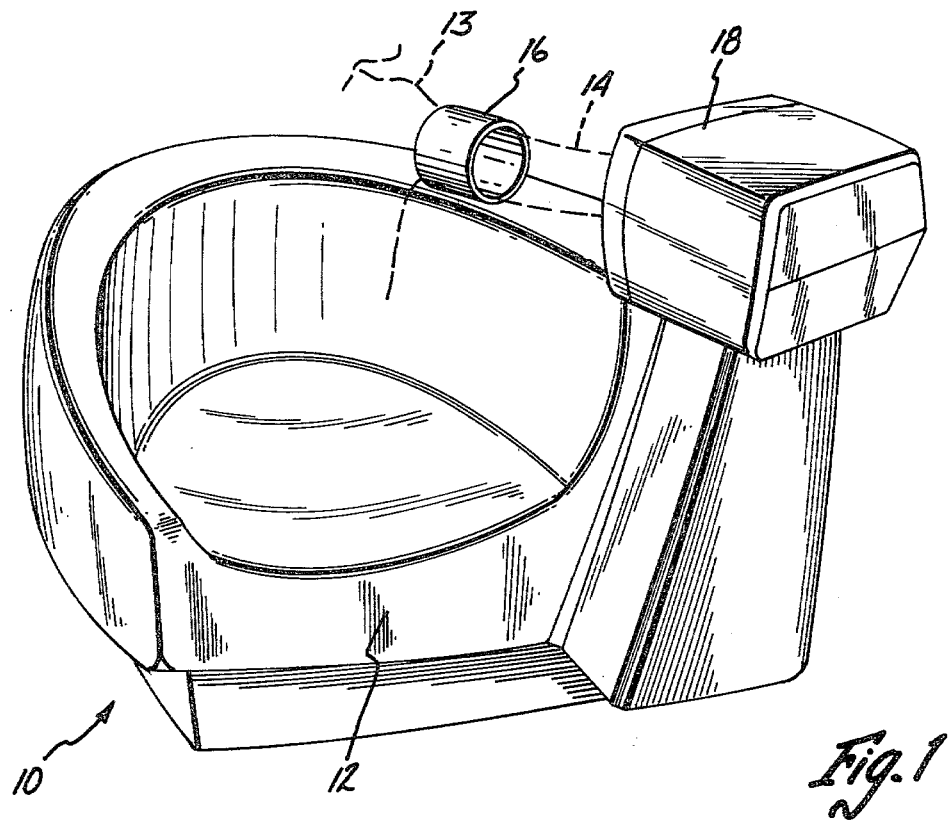
FIG. 1 is a perspective view showing an automatic blood pressure measuring apparatus.

FIG. 1 shows blood pressure measuring apparatus 10 which includes a chair portion 12 in which a person 13 (partially shown, in phantom) sits while his or her blood pressure is measured. The person places one arm 14, shown in phantom in FIG. 1, into an inflatable cuff mechanism 16.

Figure 2:
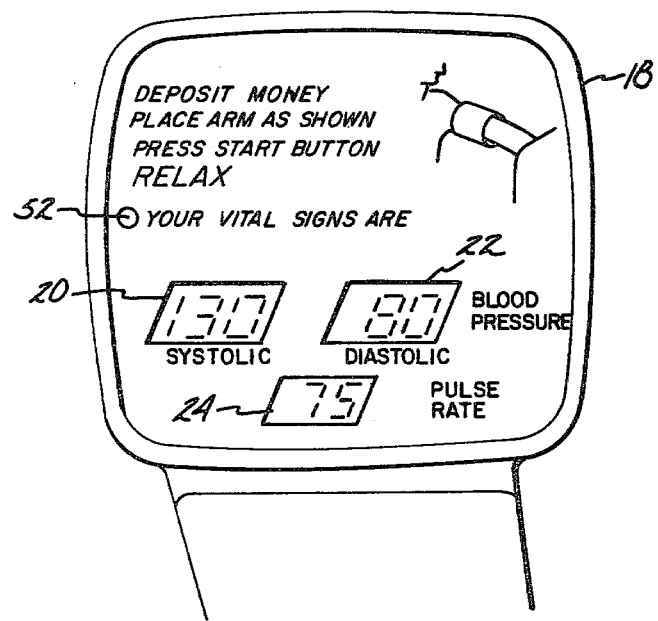
FIG. 2 shows a display panel of the automatic blood pressure measuring apparatus of FIG. 1.

Upon initiation of operation, the inflatable portion of cuff 16 is tightened by a motor (not shown in FIG. 1) and is inflated around arm 14 by means of a pump (not shown in FIG. 1). Cuff 16 then slowly releases its pressure until a microphone inside cuff 16 picks up the Korotkoff sounds which indicate systolic and then diastolic pressures. As shown in FIGS. 1 and 2, display panel 18 faces the person in chair 12 and includes three digit displays 20, 22 and 24 which display the systolic pressure, diastolic pressure and pulse rate of the person based upon the measurements made as the cuff pressure was released.

Figure 3:
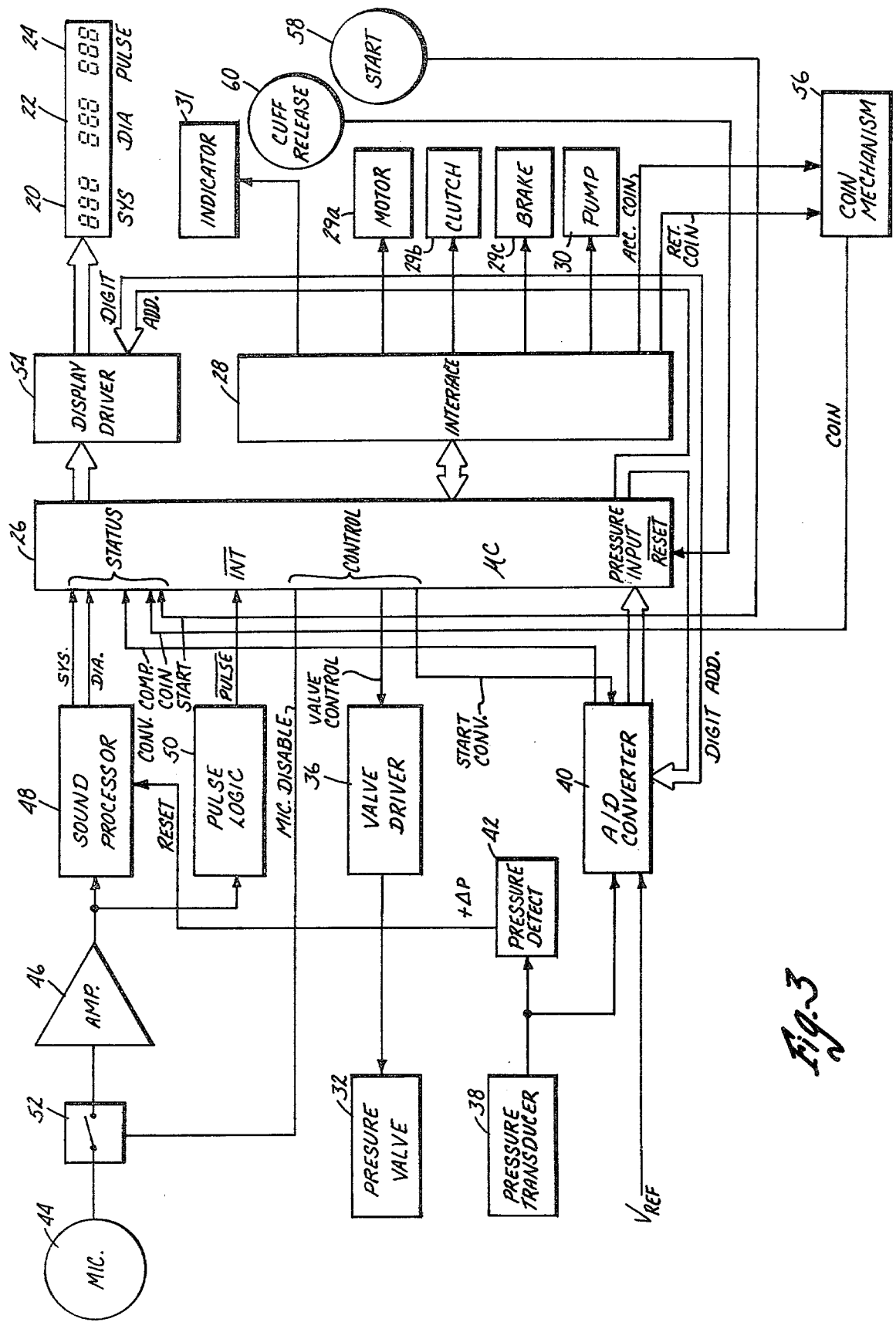
FIG. 3 is an electrical block diagram of a preferred embodiment of the automatic blood pressure measuring apparatus of the present invention.

FIG. 3 is an electrical block diagram of a preferred embodiment of the blood pressure measuring apparatus of the present invention. As shown in FIG. 3, operation of the blood pressure measuring apparatus is controlled by microcomputer 26, which is preferably an eight-bit microcomputer such as an Intel 8048 or 8748 integrated circuit. Microcomputer 26 controls, through interface circuit 28, a motor 29a, clutch 29b, brake 29c and pump 30 for tightening down and inflating cuff 16 so as to occlude arterial flow in arm 14 of the person whose blood pressure is being tested. In addition, microcomputer 26 controls indicator 31 through interface 28.

Once cuff 16 is inflated to the desired pressure, the air within cuff 16 is gradually released by pressure relief valve 32. Microcomputer 26 controls valve 32 by supplying a VALVE CONTROL signal to valve driver 36.

Pressure transducer 38 measures the pressure in cuff 16, and provides an analog signal to A/D converter 40. The output of A/D converter 40 is a pressure input supplied to microcomputer 26. A/D converter 40 provides a digital pressure output signal by comparing the analog signal from pressure transducer 38 with a reference voltage $V_{REF}$. Operation of A/D converter 40 is initiated by a START CONVERSION signal from microcomputer 26. A/D converter 40 provides a CONVERSION COMPLETE signal to a status input of microcomputer 26 to indicate when a conversion of the analog signal to a digital pressure signal has been completed.

Also shown in FIG. 3 is a delta pressure detect circuit 42 which receives the analog output of pressure transducer 38 and detects when the pressure is increasing rapidly. This condition occurs at the beginning of a cycle, when pump 30 is operating. As a result, delta pressure detect circuit 42 provides reset signals during the operation of pump 30. During the remainder of operation of the pressure measuring apparatus, delta pressure detect circuit 42 is inactive.

Microphone 44 is located within cuff 16 in a position over the brachial artery in arm 14. The output of microphone 44 is amplified and conditioned by amplifier and signal conditioner circuit 46. The output of circuit 46 is supplied to a Korotkoff sound processor 48 and pulse logic 50. The output of Korotkoff sound processor 48 consists of a SYS signal and a DIA signal. These two signals are supplied to status inputs of microcomputer 26 and indicate the occurrence of the systolic and diastolic events, respectively. The output of pulse logic 50 is a $\overline{PULSE}$ signal which is supplied as an interrupt signal to microcomputer 26. Korotkoff sound processor 48 receives the RESET signal from delta pressure detect circuit 42.

Microcomputer 26 controls microphone disable switch 52, which is connected between microphone 44 and amplifier and signal conditioner 46 by means of a MICROPHONE DISABLE signal. In one embodiment, microphone disable switch 52 is an analog switch such as a FET.

The outputs of the apparatus are the systolic pressure displayed on three-digit display 20, the diastolic pressure displayed by three-digit display 22, and the pulse rate displayed by three-digit display 24. Displays 20, 22 and 24 are controlled by microcomputer 26 through display driver 54. Display driver 54 is addressed by microcomputer 26 through digital address lines.

In the preferred embodiment shown in FIG. 3, the automatic blood pressure measuring apparatus is coin operated. Microcomputer 26 receives a COIN signal from coin mechanism 56 when appropriate coins have been deposited. Microcomputer 26 also supplies ACCEPT COIN and RETURN COIN signals to coin mechanism 56.

Operation of the apparatus of FIG. 3 during a normal operation cycle is as follows: microcomputer 26 constantly monitors the status of the COIN signal from coin receiver 56. In addition, microcomputer 26 monitors the value of the digital PRESSURE signal applied by A/D converter 40 based upon the pressure measurement by pressure transducer 38. During this time period, the inflatable portion of cuff 16 is deflated, so that it is at its minimum pressure. Whatever value is received from A/D converter 40 represents an initial offset value which is used to correct all pressure readings taken during an active operating cycle.

When person 13 sits in chair 12 and deposits a coin or coins in coin receiver 56, the COIN signal is supplied to microcomputer 26 and causes microcomputer 26 to actuate indicator 31. Microcomputer 26 then waits for person 13 to depress start button 58 to supply a START signal which will begin the actual measurement cycle. If the person who deposited the coins changes his mind and decides not to use the apparatus, he may depress the cuff release button 60, which provides a reset signal to microcomputer 26. This causes the apparatus to return to its original standby condition, with the cuff deflated and released. In this case, microcomputer 26 supplies the RETURN COIN signal to coin mechanism 56.

In a normal cycle, the person who deposited the coins does depress start button 58. Microcomputer 26 then actuates motor 29a and clutch 29b, which pulls the inflatable portion of cuff 16 down around the person's arm. When the inflatable portion of cuff 16 is sufficiently tight, or after a predetermined time period (whichever comes first), microcomputer 26 supplies the signals to motor 29a, clutch 29b and brake 29c which causes inflatable cuff 16 to be clamped or locked in place around arm 14. Microcomputer 26 then turns on pump 30.

Pump 30 rapidly inflates cuff 16 up to a predetermined pressure, which in one preferred embodiment is about 180 mm Hg. Pressure transducer 38 monitors the pressure during operation of pump 30, and supplies an output signal to both A/D converter 40 and delta pressure detect circuit 42. The rapid increase in pressure caused by operation of pump 30 causes delta pressure detect circuit 42 to supply a RESET signal to Korotkoff sound processor 48 to reset status bits in preparation for the new measurement cycle which is about to begin.

When the pressure signal from an A/D converter 40 indicates that the pressure has reached 180 mm Hg, microcomputer 26 turns off pump 30. At this point, microcomputer 26 enables microphone 44 and monitors the $\overline{\text{PULSE}}$ interrupt signal from pulse logic 50. If a pressure of 180 mm Hg has occluded the brachial artery in arm 14, no $\overline{\text{PULSE}}$ signals will be received, since microphone 44 will not sense any blood flow pulses in the brachial artery. If, on the other hand, the brachial artery is not totally occluded at 180 mm Hg cuff pressure, microphone 44 detects sound and the $\overline{\text{PULSE}}$ interrupt signal is supplied to microcomputer 26. In this case, microcomputer 26 again turns on pump 30 and increases the cuff pressure to a higher value, such as 220 mm Hg. At this point microcomputer 26 again turns off pump 30 and begins to monitor the $\overline{\text{PULSE}}$ signal. If microcomputer 26 again receives a $\overline{\text{PULSE}}$ signal, it does not activate pump 30 again, since higher cuff pressures could cause injury to a person's arm.

Assuming that the brachial artery is occluded at either 180 mm Hg or at 220 mm Hg, the apparatus then goes into a search mode. In this mode, microcomputer 26 periodically at intervals of about 1.25 seconds, supplies signals to valve driver 36 to open pressure relief valve 32 for a time period sufficient to cause a decrease of about 3 mm Hg pressure.

Because the pressure is decreasing each time that pressure relief valve 32 is opened, pressure valve 32 must be opened for longer and longer periods of time in order to maintain a constant incremental 3 mm Hg pressure drop. The apparatus of the present invention automatically maintains the incremental pressure drop at approximately 3 mm Hg by sensing the cuff pressure before and after each valve opening and closing by means of pressure transducer 38. After each time that valve 32 has been opened and closed, microcomputer 26 compares the current and preceding pressure readings from pressure transducer 38. Microcomputer 26 then calculates the time duration of the next opening of valve 32 so as to maintain the average incremental pressure decrease at approximately 3 mm Hg. In other words, if a comparison of the pressure readings before and after an opening of pressure valve 32 indicates that a drop of greater than 3 mm Hg has occurred, the next valve opening duration is reduced by microcomputer 26 so that the average decrease of 3 mm Hg is maintained.

During the search mode, microcomputer 26 first disables microphone 44 by opening switch 52, and then opens pressure valve 32. Switch 52 remains open and microphone 44 remains disabled until after valve 32 has again been closed. It has been found that there is a large amount of transient noise caused by the opening and closing of pressure valve 32. In effect, the opening of valve 32 sets up shock waves which could cause false signals to be sensed by microphone 44.

As long as the search mode continues, switch 52 is opened (and microphone 44 is disabled) approximately every 1.25 seconds and the valve is opened and then closed during the time that switch 52 is open. If no $\overline{\text{PULSE}}$ signal is received by microcomputer 26 during the 1.25 second time period, microcomputer 26 commences another valve opening cycle. The time period of approximately 1.25 seconds represents a period of time in which a pulse should be detected if the systolic pressure has been reached. If a pulse is not detected, it indicates systolic pressure has not yet been obtained, and the search mode continues.

Eventually, the cuff pressure is reduced to a level at which blood begins to flow through the brachial artery. This represents the systolic pressure, and is detected by Korotkoff sound processor 48. In addition, the pulse sound of the blood flow is detected by pulse logic 50, which supplies the $\overline{\text{PULSE}}$ signal to microcomputer 26. Once this has occurred, the apparatus shifts to a mode in which it is synchronized to the pulse beats of the person. In other words, microcomputer 26 no longer waits the full 1.25 seconds between successive valve opening cycles. Rather, each valve opening cycle is triggered in response to a $\overline{\text{PULSE}}$ signal.

The decision by Korotkoff sound processor 48 that the systolic pressure has been attained is preferably based upon a ratio of two amplitudes, in a manner similar to that shown in the previously mentioned Fletcher et al U.S. Pat. No. 3,814,083. In a preferred embodiment of the present invention, this decision by Korotkoff sound processor 48 is verified by waiting a predetermined time period (such as 1.25 seconds) during which another pulse should be detected if true systolic pressure has been attained. If another pulse is not detected within that time period, it can be assumed that actual systolic pressure has not yet been attained. In a preferred embodiment, Korotkoff sound processor 48 includes a flipflop which is set when the sound processor identifies systolic pressure. If another valid pulse is not detected within 1.25 seconds of when the flipflop was set, the flipflop is automatically reset.

The SYS signal supplied by Korotkoff sound processor 48 is, therefore, verified by the occurrence of a second pulse within a 1.25 second time period after a first pulse is detected and identified as indicative of the occurrence of the systolic event. As a result, of course, the SYS signal is supplied to microcomputer 26 one pulse after systolic pressure was actually attained. In that time period, pressure relief valve 32 has again been opened, so that the pressure reading at the time that the SYS signal is supplied is lower than the actual systolic pressure. Microcomputer 26 compensates for this time delay by storing the immediately preceding pressure reading, as well as the current pressure reading. When the SYS signal is received, microcomputer 26 retrieves the preceding pressure reading, and calculates the systolic pressure based upon the preceding pressure reading. In the embodiment of the present invention shown in FIG. 3, the systolic pressure is not immediately displayed on display 20, but rather is stored until the diastolic pressure and the pulse rate have also been calculated. In this manner, all three values are displayed simultaneously after the measurement cycle is completed.

Upon receiving the SYS signal, microcomputer 26 begins counting the $\overline{\text{PULSE}}$ signals which are received. In addition, microcomputer 26 begins counting the time elapsed since receipt of the SYS signal. The counting of $\overline{\text{PULSE}}$ signals and the counting of elapsed time continues until Korotkoff sound processor 48 supplies the DIA signal indicative of the occurrence of the diastolic pressure. At that time, microcomputer 26 has the necessary information to calculate a pulse rate which will be displayed on display 24.

The detection of the diastolic pressure and the production of the DIA signal is similar to the production of the SYS signal, in that it requires a verification before the DIA signal is produced. In a preferred embodiment, Korotkoff sound processor 48 includes a flipflop which is set when diastolic pressure is identified. If another pulse is detected within 1.25 seconds, the flipflop is reset and the DIA signal is not produced. If, on the other hand, no pulse is sensed during the 1.25 second time period, then the DIA signal is produced and supplied to a status input of interface circuit 34. As in the case of the SYS signal, the DIA signal is delayed in time with respect to the pressure reading. Microcomputer 26 determines the correct diastolic pressure by retrieving the preceding pressure reading and calculating the diastolic pressure.

Once the systolic and diastolic pressures and the pulse rate have been calculated, the measurement cycle is completed. Microcomputer 26 supplies signals to display driver 54, causing the systolic pressure, the diastolic pressure and the pulse rate to be displayed. Microcomputer 26 then opens pressure valve 32 to deflate cuff 16 completely and supplies the appropriate signals to motor 29a, clutch 29b and brake 29c to release the cuff.

It is highly advantageous, of course, for microphone 44, amplifier and signal conditioner 46, Korotkoff sound processor 48, and pulse logic 50 to be as sensitive as possible. On the other hand, noise must be removed so that pulses are not incorrectly identified. The present invention provides the desired sensitivity, while removing noise and other artifacts.

Figure 4:
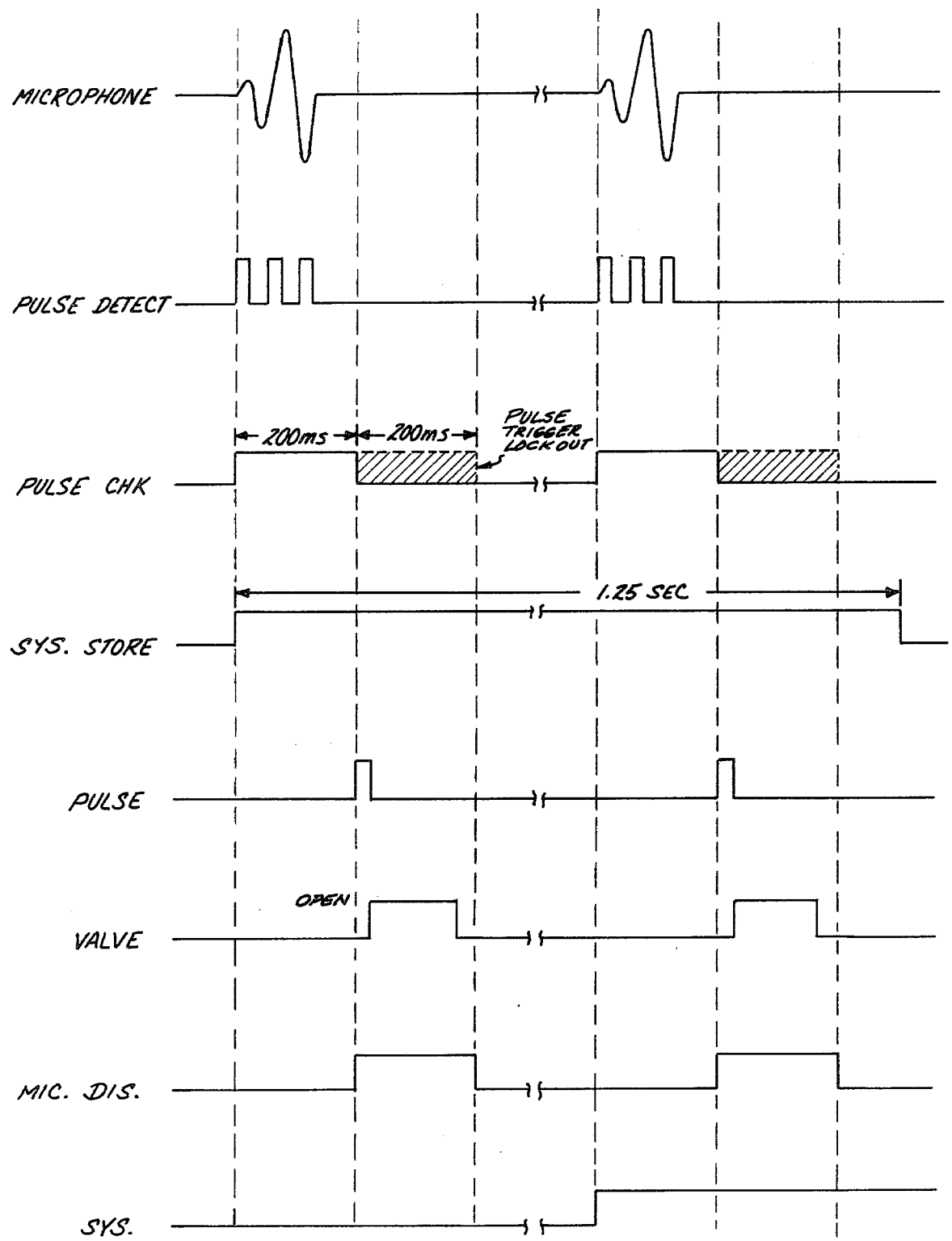
FIG. 4 shows waveforms produced within the blood pressure measuring apparatus of FIG. 3.

FIG. 4 is a timing diagram illustrating the signals generated during operation of the apparatus of FIG. 3. FIG. 4 illustrates these signals for the first two pulses which are detected. In other words, the first pulse represents the systolic event. As described previously, upon detection of the first pulse, the system goes into a pulse triggered mode, rather than the search mode which has been used to locate the systolic pressure.

The first signal shown in FIG. 4 is the MICROPHONE signal, which is the output of microphone 44. This signal is processed and amplified by amplifier and signal conditioner 46. The PULSE DETECT signal shown in FIG. 4 is normally a logic low level, but goes high with each positive excursion of the MICROPHONE signal. As a result, the PULSE DETECT signal goes high several times for a single pulse sensed by microphone 44. The PULSE CK signal shown in FIG. 4 represents the debounced pulse and has a duration of 200 milliseconds. The PULSE CK signal initially goes high when the PULSE DETECT signal first goes high and remains high for 200 milliseconds.

Upon the occurrence of the first PULSE DETECT signal, the SYS STORE signal goes high and remains high for a duration of 1.25 seconds. THE SYS STORE signal is a timing signal used to verify that true systolic pressure has been detected. If another pulse does not occur within the 1.25 second time duration of the SYS STORE signal, it is assumed that true systolic pressure has not occurred. As shown in FIG. 4, true systolic pressure has been sensed, since another pulse is detected by microphone 44 within the 1.25 second time period. Upon the occurrence of the second pulse within the 1.25 second time period during which the SYS STORE signal is high, the SYS output of Korotkoff sound processor 48 goes high, as shown in FIG. 4.

When the PULSE CK signal goes low, the $\overline{\text{PULSE}}$ signal is supplied as an interrupt to microcomputer 26. The occurrence of the $\overline{\text{PULSE}}$ signal going high causes microcomputer 26 to supply the MICROPHONE DISABLE signal which turns off microphone 44. Upon the $\overline{\text{PULSE}}$ signal going low, microcomputer 26 supplies signals to valve logic and driver 36 which opens valve 32. As shown in FIG. 4, the MICROPHONE DISABLE signal remains high, thereby opening switch 52 and disabling microphone 44 until after valve 32 has again closed. The purpose of the MICROPHONE DISABLE signal is to prevent microphone 44 from picking up noise associated with the opening and closing of valve 32 and supplying false signals to amplifier 46.

In addition to the MICROPHONE DISABLE signal, the system further prevents false signals due to valve noise by a pulse trigger lockout which is shown as a 200 millisecond shaded area following the PULSE CK signal. This pulse trigger lockout is not generated by microcomputer 26, but rather is hardware generated within amplifier and signal conditioner 46. This prevents any other signals from being generated during the time when valve 32 is being opened and closed.

It can be seen, therefore, that the present invention prevents valve 32 from being opened while signal processing has occurred, and prevents signals from being generated while the valve 32 is being opened and closed. As a result, problems due to noise generated by opening and closing of valve 32 are minimized.

In conclusion, the present invention is a highly effective automatic blood pressure measuring system which determines not only the systolic and diastolic pressures, but also the pulse rate of an individual. The present invention, in the preferred embodiments described, automatically maintains essentially constant incremental decreases in pressure during the blood pressure measuring operation, thereby leading to more accurate blood pressure measurements. In addition, operation of the pressure relief valve and the signal processing circuitry is synchronized to avoid noise problems.

Although the present invention has been described with reference to preferred embodiments, workers skilled in the art will recognize that changes may be made in form and detail without departing from the spirit and scope of the invention.

What is claimed is:

1. A noninvasive blood pressure measuring apparatus comprising:

an inflatable cuff for encircling a portion of the human body;

means for inflating the inflatable cuff to a pressure sufficient to occlude arterial flow;

pressure relief valve means for deflating the cuff;

pressure sensor means for sensing the pressure within the cuff and providing digital pressure values as a function of the sensed pressure within the cuff; and means for controlling the time duration of each opening of the pressure relief valve means as a function of the sensed pressure before a previous opening of the pressure reflief valve means and the sensed pressure after the previous opening of the pressure relif valve means, wherein the means for controlling the time duration comprises digital computer means for computing a time duration of each opening of the pressure relief valve means as a function of the digital pressure values before and after a previous opening of the pressure relief valve means.

2. The system of claim 1 wherein the means for controlling the time duration of each opening comprises:

means for providing a first signal which causes the pressure relief valve means to open;

means for providing a second signal which causes the pressure relief valve means to close; and means for controlling the time duration between the first and second signals as a function of the sensed pressure before a previous opening of the pressure relief valve means and the sensed pressure after the previous opening of the pressure relief valve means.

3. The invention of claim 2 wherein means for controlling the time duration between the first and second signals compares the difference between the sensed pressures before and after the previous opening of the pressure relief valve means and controls the time duration to maintain a desired average decrease in pressure per valve opening.

4. The invention of claim 1 wherein the means for controlling the time duration further comprises:
   valve driver means for driving the pressure relief valve means in response to signals from the digital computer means.

5. The invention of claim 4 wherein the digital computer means provides signals to the valve driver means to cause the valve driver means to open the pressure relief valve means and, after the time duration computed by the digital computer means, to close the pressure relief valve means.

6. The invention of claim 5 and further comprising:
   sound monitoring means for monitoring sounds of arterial flow past the cuff and producing electrical signals in response to the sounds;
   Korotkoff sound processor means for receiving electrical signals and providing a systolic event indicative of occurrence of a systolic event and a diastolic event indicative of occurrence of a diastolic event;
   pulse signal producing means for receiving the electrical signals and providing a pulse interrupt signal to the digital computer means, the pulse interrupt signal being indicative of occurrence of each arterial flow pulse;
   means for displaying the systolic and diastolic pressures; and
   wherein the digital computer means computes the systolic pressure as a function of a first sensed pressure associated with occurrence of the systolic event computes the diastolic pressure as a function of a second sensed pressure associated with occurrence of the diastolic event, and provides signals to the display means causing the display means to display the systolic and diastolic pressures.

7. The invention of claim 6 wherein the digital computer means provides signals to the valve driver means to cause the pressure relief valve means to open at predetermined time intervals during a first time period after inflation of the cuff and prior to receiving a pulse interrupt signal, and causing the pressure relief valve means to open in response to the pulse interrupt signals during a second time period after a pulse interrupt signal has been received.

8. The invention of claim 7 wherein the digital computer means provides a disable signal to the sound monitoring means to prevent production of electrical signals during a predetermined time interval, and provides signals to the valve driver means to open the pressure relief valve means only during the predetermined time interval.

9. The invention of claim 8 wherein the time duration of each opening of the pressure relief valve is less than the predetermined time interval during which production of electrical signals is prevented.

10. The invention of claim 6 wherein the digital computer means counts the number of pulse interrupt signals provided between occurrence of the systolic event and the diastolic event signal, determines the time elapsed between the occurrence of the systolic event and diastolic event signals, and calculates a pulse rate based upon the number of pulse signals and the time elapsed; and wherein the display means further displays the calculated pulse rate.

11. The invention of claim 6 and further comprising: means for providing a reset signal to the Korotkoff sound processor means in response to a sensed increase in pressure within the cuff indicative of inflation of the cuff.

12. The invention of claim 6 wherein the pressure sensor means provides a digital pressure value prior to the inflation of the cuff, and wherein the digital computer means stores the pressure value and corrects subsequent pressure values during deflation of the cuff based upon the stored pressure value.

13. A noninvasive blood pressure monitoring apparatus comprising:
   an inflatable cuff for encircling a portion of the human body;
   means for inflating the inflatable cuff to a pressure sufficient to occlude arterial flow;
   pressure relief valve means for deflating the cuff by increments;
   pressure sensor means for sensing the pressure within the cuff;
   means for controlling the time duration of each opening of the pressure relief valve means as a function of an incremental decrease in pressure resulting from a preceding opening of the pressure relief valve means;
   sound monitoring means for monitoring sounds of arterial flow past the cuff and producing electrical signals in response to the sounds;
   Korotkoff sound processor means for receiving the electrical signals and providing a systolic event signal indicative of occurrence of a systolic event and a diastolic event signal indicative of occurrence of a diastolic event;
   pulse signal producing means for receiving the electrical signals and providing a pulse signal indicative of occurrence of each arterial flow pulse;
   means for providing a signal indicative of the systolic pressure as a function of a first sensed pressure associated with the occurrence of the systolic event signal;
   means for providing a signal indicative of the diastolic pressure as a function of a second sensed pressure associated with occurrence of the diastolic event;
   means for opening the pressure relief valve means at predetermined time intervals prior to production of a pulse signal, and for opening the pressure relief valve means in response to the pulse signals after a pulse signal has been produced;
   means for providing a disable signal to the sound monitoring means to prevent production of electrical signals during a predetermined time period; and
   wherein means for opening the pressure relief valve means opens the pressure relief valve means only during the predetermined time period.

14. The invention of claim 13 wherein the time duration of each opening of the pressure relief valve is less than the predetermined time period during which production of electrical signals is prevented.

15. The apparatus of claim 13 and further comprising: means for providing a reset signal to the Korotkoff sound processor means in response to a sensed increase in pressure within the cuff indicative of inflation of the cuff.

16. A noninvasive blood pressure and pulse rate measuring apparatus comprising:
an inflatable cuff for encircling a portion of the human body;
means for inflating the cuff to a pressure sufficient to occlude arterial flow;
pressure relief valve means for deflating the cuff by increments over a period of time sufficient to permit systolic and diastolic events to occur;
sound monitoring means for monitoring sounds of arterial flow past the cuff and producing electrical signals in response to the sounds;
means for providing a disable signal to the sound monitoring means to prevent production of electrical signals during a predetermined time period, and for causing the pressure relief valve means to open only during the predetermined period;
means for providing a systolic event signal indicative of occurrence of the systolic event;
means for supplying a diastolic event signal indicative of occurrence of the diastolic event;
means for providing a pulse signal indicative of occurrence of each arterial flow pulse;
means for determining the time elapsed between occurrence of the systolic event and diastolic event signals;
means for counting the number of pulse signals provided between the occurrence of the systolic event signal and the occurrence of the diastolic event signal;
means for sensing the pressure in the inflatable cuff;
means for providing a signal indicative of the systolic pressure as a function of a first sensed pressure and the occurrence of the systolic event signal; and
means for providing a signal indicative of pulse rate based upon the number of pulse signals counted and the time elapsed between occurrence of the systolic event and diastolic event signals.

17. A noninvasive blood pressure monitoring apparatus comprising:
an inflatable cuff for encircling a portion of the human body;
means for inflating the inflatable cuff to a pressure sufficient to occlude arterial flow;
pressure relief valve means for deflating the cuff by increments;
pressure sensor means for sensing the pressure within the cuff;
sound monitoring means for monitoring sounds of arterial flow past the cuff and producing electrical signals in response to the sounds;
Korotkoff sound processor means for receiving the electrical signals and providing a systolic event signal indicative of occurrence of a systolic event and a diastolic event signal indicative of occurrence of a diastolic event;
pulse signal producing means for receiving the electrical signals and providing a pulse interrupt signal indicative of occurrence of each arterial flow pulse;
digital computer means for receiving the systolic, diastolic and pulse interrupt signals and pressure readings from the pressure sensor means and calculating systolic pressure and diastolic pressure, the digital computer means controlling the pressure relief valve means to cause the pressure relief valve means to open at predetermined time intervals during a first time period prior to receiving a pulse interrupt signal, and for causing the pressure relief valve means to open in response to each pulse interrupt signal during a second time period after a pulse interrupt signal has been received, wherein the digital computer means provides a disable signal to the sound monitoring means to prevent production of electrical signals during a predetermined time period, and causes the pressure relief valve means to open only during the predetermined period.

18. The invention of claim 17 wherein the digital computer means calculates a pulse rate based upon time elapsed and number of pulse interrupt signals received between occurrence of the systolic and diastolic event signals.

* * * * *